(12) United States Patent
Wieting et al.

(10) Patent No.: US 10,369,265 B2
(45) Date of Patent: *Aug. 6, 2019

(54) METHOD AND APPARATUS FOR REMOVAL OF GAS BUBBLES FROM FLUID

(71) Applicant: Indian Wells Medical, Inc., Laguna Beach, CA (US)

(72) Inventors: David W. Wieting, Sierra Madre, CA (US); Jay A. Lenker, Laguna Beach, CA (US)

(73) Assignee: Indian Wells Medical, Inc., Laguna Beach, CA (US)

( * ) Notice: Subject to any disclaimer, the term of this patent is extended or adjusted under 35 U.S.C. 154(b) by 177 days.

This patent is subject to a terminal disclaimer.

(21) Appl. No.: 15/421,197

(22) Filed: Jan. 31, 2017

(65) Prior Publication Data

US 2017/0136170 A1    May 18, 2017

Related U.S. Application Data

(63) Continuation of application No. 14/607,015, filed on Jan. 27, 2015, now Pat. No. 9,555,182, which is a
(Continued)

(51) Int. Cl.
*A61M 1/36* (2006.01)
*A61M 5/36* (2006.01)
(Continued)

(52) U.S. Cl.
CPC ........ *A61M 1/3633* (2013.01); *A61M 1/1658* (2013.01); *A61M 1/3627* (2013.01); *A61M 1/3666* (2013.01); *A61M 1/3667* (2014.02); *A61M 5/36* (2013.01); *B01D 19/0031* (2013.01); *B01D 19/0057* (2013.01); *B01D 19/0094* (2013.01); *B04C 3/00* (2013.01); *B04C 3/06* (2013.01); *B04C 5/02* (2013.01); *B04C 5/04* (2013.01); *B04C 5/08* (2013.01); *B04C 5/107* (2013.01); *B04C 9/00* (2013.01); *A61M 1/3626* (2013.01); *A61M 2205/75* (2013.01);
(Continued)

(58) Field of Classification Search
CPC .............. A61M 1/1658; A61M 1/3626; A61M 1/3627; A61M 1/3633; A61M 1/3666; A61M 1/3667; A61M 2205/75; A61M 2205/7527; A61M 2206/16; A61M 5/36; B01D 19/0031; B01D 19/0057; B01D 19/0094; B01D 2247/10; B01D 2247/101; B01D 2247/108; B04C 2009/004; B04C 2009/007; B04C 3/00; B04C 3/06; B04C 5/02; B04C 5/04; B04C 5/08; B04C 5/107; B04C 9/00
See application file for complete search history.

(56) References Cited

U.S. PATENT DOCUMENTS 3,996,027 A * 12/1976 Schnell ............... A61M 1/3627
95/261
4,209,359 A *  6/1980 Sethy ................. B01D 19/0052
162/29
(Continued)

*Primary Examiner* — Adam Marcetich
(74) *Attorney, Agent, or Firm* — K. David Crockett, Esq.; Crockett & Crockett, PC

(57) ABSTRACT

A system and method for removing gas bubbles from fluid. An active filter apparatus forces the bubbles to the center of the filter, while a pump supplies fluid to the filter.

19 Claims, 5 Drawing Sheets

Related U.S. Application Data continuation of application No. 13/903,241, filed on May 28, 2013, now Pat. No. 8,939,926, which is a continuation of application No. 12/925,922, filed on Nov. 2, 2010, now Pat. No. 8,480,606, which is a continuation of application No. 12/322,594, filed on Feb. 4, 2009, now Pat. No. 7,824,356, which is a continuation of application No. 10/791,075, filed on Mar. 1, 2004, now Pat. No. 7,488,448.

(51) Int. Cl.
| | |
|---|---|
| *B01D 19/00* | (2006.01) |
| *B04C 3/06* | (2006.01) |
| *B04C 5/04* | (2006.01) |
| *B04C 5/107* | (2006.01) |
| *B04C 9/00* | (2006.01) |
| *A61M 1/16* | (2006.01) |
| *B04C 5/08* | (2006.01) |
| *B04C 5/02* | (2006.01) |
| *B04C 3/00* | (2006.01) |

(52) U.S. Cl.
CPC . *A61M 2205/7527* (2013.01); *A61M 2206/16* (2013.01); *B01D 2247/10* (2013.01); *B01D 2247/101* (2013.01); *B01D 2247/108* (2013.01); *B04C 2009/004* (2013.01); *B04C 2009/007* (2013.01)

(56) References Cited

U.S. PATENT DOCUMENTS

| | | | | |
|---|---|---|---|---|
| 4,936,759 A | * | 6/1990 | Clausen | A61M 1/3627 128/DIG. 3 |
| 4,994,097 A | * | 2/1991 | Brouwers | B01D 45/14 55/317 |
| 5,470,465 A | * | 11/1995 | Moorehead | B03D 1/1418 209/12.2 |
| 5,632,894 A | * | 5/1997 | White | A61M 1/3627 210/436 |
| 5,711,753 A | * | 1/1998 | Pacella | A61M 1/101 600/16 |
| 5,853,456 A | * | 12/1998 | Bryan | A61M 1/3627 95/30 |
| 5,961,700 A | * | 10/1999 | Oliver | A61M 1/3627 210/188 |
| 6,066,111 A | * | 5/2000 | Brockhoff | A61M 1/0039 210/787 |
| 6,261,330 B1 | * | 7/2001 | Dyson | A47L 9/1608 55/345 |
| 6,629,821 B1 | * | 10/2003 | Yokota | F04D 9/003 417/199.1 |
| 7,108,785 B1 | * | 9/2006 | Plechinger | A61M 1/3627 210/188 |
| 2001/0032812 A1 | * | 10/2001 | Morse | B01D 19/0042 210/257.1 |
| 2002/0110485 A1 | * | 8/2002 | Stringer | A61M 1/3626 422/45 |
| 2002/0114731 A1 | * | 8/2002 | Stringer | A61M 1/101 422/44 |
| 2003/0024873 A1 | * | 2/2003 | Klass | B01D 45/14 210/512.3 |
| 2003/0152462 A1 | * | 8/2003 | Yaegashi | F04D 29/048 417/42 |
| 2004/0256312 A1 | * | 12/2004 | Gomez | B01D 19/0052 210/512.3 |
| 2005/0247203 A1 | * | 11/2005 | Chevallet | A61M 1/3627 96/209 |

\* cited by examiner

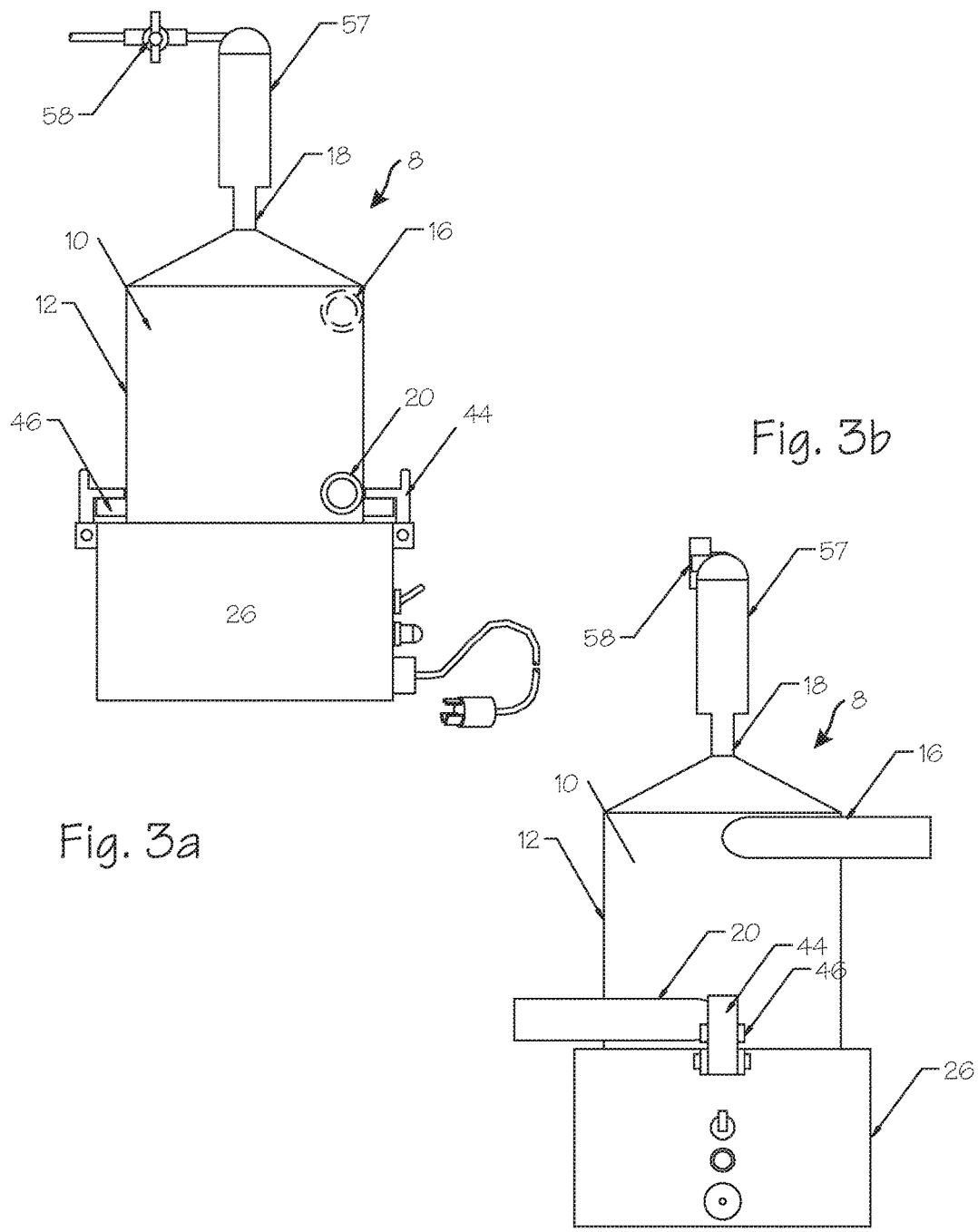

METHOD AND APPARATUS FOR REMOVAL OF GAS BUBBLES FROM FLUID

This application is a continuation of U.S. application Ser. No. 14/607,015, filed Jan. 27, 2015, now U.S. Pat. No. 9,555,182, which is a continuation of U.S. application Ser. No. 13/903,241, filed May 28, 2013, now U.S. Pat. No. 8,939,926, which is a continuation of U.S. application Ser. No. 12/925,922, filed Nov. 2, 2010, now U.S. Pat. No. 8,480,606, which is a continuation of U.S. application Ser. No. 12/322,594, filed Feb. 4, 2009, now U.S. Pat. No. 7,824,356, which is a continuation of U.S. application Ser. No. 10/791,075, filed Mar. 1, 2004, now U.S. Pat. No. 7,488,448.

FIELD OF THE INVENTION

The field of this invention is cardiac circulatory assist and, more specifically, cardiopulmonary bypass.

BACKGROUND OF THE INVENTION

During cardiovascular surgical procedures, the heart is often arrested and the patient is placed on cardiopulmonary bypass. In addition, a subset of patients with cardiopulmonary complications and or disease will be placed on partial longer-term cardiopulmonary bypass. These patients include, but are not limited to: neonates with severe pulmonary lung disease, bridge to transplant patients, liver transplant patients and patients with severe myocardial trauma accompanied by pump failure. Such cardiopulmonary bypass is used to support the patient's circulation and/or pulmonary function while the heart is being surgically repaired or the failing organ is allowed to recover. Typical surgical repair procedures include valve replacement, annuloplasty, coronary artery bypass grafting, total heart replacement, cardiac assist placement, repair of tetralogy of Fallot, repair of atrial and ventricular septal defects, heart and/or lung transplantation, liver transplantation and the like. Cardiopulmonary bypass devices use a cannula to remove blood from the patient where it is oxygenated, purged of carbon dioxide, heated or cooled, filtered and pumped back into the systemic circulation of the patient. Blood filters are used in the cardiopulmonary bypass system to trap particulates and gas bubbles that are generated in the extracorporeal loop. Blood filters prevent particulates and gas bubbles from being pumped back into the patient. The most common gas entrained within the blood of an extracorporeal circuit is air. Such particulates and gas bubbles, also known as emboli, can cause blockage in the arterioles and capillary beds and lead to ischemic cell death. Consequences of such ischemic cell death may affect organ function (viz. intestine, pancreas, kidney, brain, etc.) and result in sepsis, renal failure and neurological defects such as loss of memory, cognitive function, and changes in personality.

Modern blood filters do trap emboli and remove debris before they are pumped back into patients but it has been scientifically validated that small gas bubbles, primarily air, and certain particulate substances missed by these filters are returned to the patients and compromise patient recovery. Patients who undergo cardiopulmonary bypass are often subject to some degree of neurological deficit as a result of the gas bubbles and other embolic materials. This phenomenon is sometimes characterized as "Pump Head".

Current blood filters are considered to be adequate for removing larger debris and large gas bubbles from the blood, but patient outcomes would be improved if small gas bubble and particulate removal efficiencies were higher. One of the primary problems with current blood filters is that when the mesh size is increased to screen out smaller particles and bubbles, the pressure drop across the filter becomes unacceptably high at normal blood flow rates. Such unacceptably high pressure gradients can potentially cause tubing or connection failures resulting in blood leaks or air leaks into the system, either of which could be catastrophic. Typical examples of the prior art in blood filters include U.S. Pat. No. 4,919,802 to Katsura, U.S. Pat. No. 4,411,783 to Dickens et al., U.S. Pat. No. 5,279,550 to Habib et al., U.S. Pat. No. 5,5,632,894 to White et al., and U.S. Pat. No. 5,683,355 to Fini et al. These patents disclose filters and bubble traps that are static devices employing filter screens to collect the debris and bubbles.

Additionally, U.S. Pat. Nos. 4,411,783, 4,919,802, and 5,632,894 disclose use of tangential blood inflow and a gas vent at the top center of the filter to improve bubble removal. The tangential inflow generates centrifugal effects to move the bubbles to the center of the device. However, since these are not active systems, they are unable to generate the rotational velocities necessary to adequately rid the blood of small bubbles that can cause neurological defects. A recent publication by Schoenburg (Ref J Thorac Cardiovasc Surg 2003:126:1455-60) describes an air bubble trap, which incorporates a three channel helix to cause the blood to passively rotate around the axis of the tube causing the centrifugal forces to direct air bubbles to the center of the flow stream where they are evacuated via a special collection tube. None of these devices impart rotational motion using an active drive system, which can rotate the blood at much higher rates and thus generate higher separation forces on the bubbles to remove them from the blood.

New devices and methods are needed to more efficiently remove gas bubbles from the blood of a patient undergoing circulatory support without traumatizing blood elements and without unacceptably increasing the pressure drop across the filter to dangerous levels.

SUMMARY OF THE INVENTION

This invention relates to a blood filter, blood-air filter, or trap for removing air or other gas bubbles and particulate matter (both large and small) from the blood of a patient during assisted circulation. The present invention is an active device that accepts blood at its inlet, actively rotates the blood to drive the bubbles toward the center of the device under centripetal force, and allows separation of the blood from the aforementioned bubbles. More dense materials, such as blood cells, move toward the periphery of the filter or are otherwise trapped by filter meshes. The device comprises a chamber or housing with a blood inlet and a blood outlet. In addition, the chamber has a third outlet for removing gas from the blood. The device additionally comprises a stirring rod or impeller to spin the blood circumferentially within the chamber. This stirring rod or impeller is coupled to a rotary motor that generates the rotational energy necessary to separate bubbles from the blood. The present invention actively removes gas bubbles and debris from the blood, including the tiny gas bubbles and particulates which current blood filters are unable to remove. The gas bubbles have less mass than the same volume of blood, i.e. the bubbles are buoyant in blood, so that rotation causes them to move toward the center of the blood filter by centripetal force. The centripetal force accelerates the bubbles until the bubbles reach a radial velocity where the drag force balances the centrifugal force. The blood filter of the present invention is designed to remove the majority of bubbles of size greater than 7 to 10 microns in diameter in the time the blood takes to traverse the volume of the filter. Thus, this is a single-pass bubble filter for a large majority of the bubbles. The design is optimized for bubbles 7 to 10 microns in diameter or larger. Bubbles smaller than 7 to 10 microns are considered less harmful to patients than larger bubbles because they will pass through the capillary beds of the patient.

In accordance with another aspect of the invention, a method is described to remove bubbles from blood. This method includes the steps of passing the blood into a circular, axially elongate or cylindrical chamber and actively spinning the blood within the chamber at high rotational rates to move the bubbles to the center of the chamber. In a further aspect of the invention, the air is removed from the blood at the center of the chamber and the blood is drawn off along the outer periphery of the chamber where it is ultimately returned to the patient.

The present invention distinguishes over the cited prior art because it uses an active component to spin the blood to forcibly remove gas bubbles from the blood. The invention is most useful during surgery when cardiopulmonary bypass is instituted to maintain the patient on temporary cardiopulmonary support. It is also useful for removal of gas and bubbles during intravenous infusion of liquids to a patient. Patients with increased risk of pulmonary emboli are especially vulnerable during intravenous infusion and would benefit from such protection.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 3A illustrates a front exterior view of the blood filter and motor drive.

FIG. 3B illustrates a side exterior view of the blood filter and motor drive, showing the blood inlet port and blood outlet port.

DETAILED DESCRIPTION OF THE INVENTION

Figure 1:
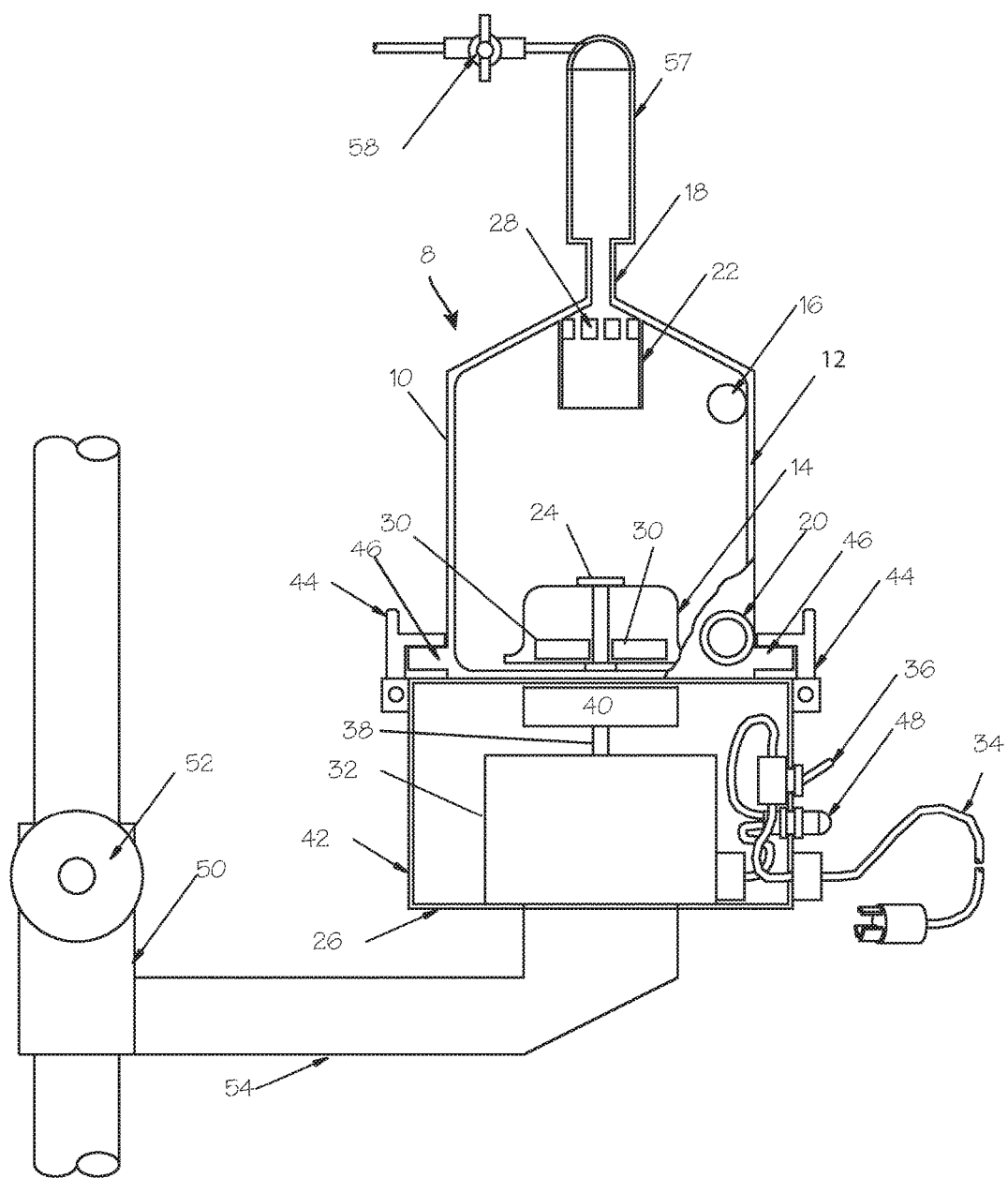
FIG. 1 illustrates a breakaway view of the blood filter of the current invention showing a cross-sectional view of the internal rotating component and the blood inflow port as well as the motor drive and pole clamp.

FIG. 1 illustrates a breakaway view of a blood filter assembly 8 of the present invention. The blood filter assembly 8 comprises a disposable blood filter 10 and a motor drive 26. The disposable blood filter 10 comprises a shell 12, an impeller 14, a blood outlet port 16, a gas outlet or central port 18, a blood inlet port 20, an optional baffle 22, and a bearing shaft 24. The optional baffle 22 optionally comprises a plurality of vent holes 28. The impeller 14 comprises a magnetic coupler 30. The shell 12 optionally comprises a plurality of lock down tabs 46, a gas trap 57 and a bleed valve 58.

The motor drive 26 comprises a motor 32, a power cable 34, a power switch 36, a central shaft 38, a magnetic driver 40, a housing 42, and a plurality of optional lock-down or clamping mechanisms 44 to hold the disposable blood filter shell 12 to the motor drive housing 42. The motor drive 26 optionally comprises a power-on lamp 48, an extension arm 54, and a pole clamp 50. The optional pole clamp 50 further comprises a setscrew 52.

The shell 12 of the disposable blood filter 10 is an axially elongate cylinder or vessel, most preferably disposed with its axis parallel to the direction of gravity. The top of the shell 12 is, preferably, conical. The gas outlet port 18 is preferably disposed along the central axis at either the top or the bottom of the shell 12. The blood inlet port 20 and the blood outlet port 16 are, preferably located on the periphery of the shell 12. The blood inlet port 20 may be located lower or higher on the periphery of the shell 12 than the blood outlet port 16 but the gas outlet port 18, otherwise known as a gas vent, is most preferably located higher than the blood inlet port 20 and the blood outlet port 16. The gas outlet port 18 is located at the entrance of the gas trap 57 and the bleed valve 58 is located at or near the highest point of the gas trap 57. The gas outlet port 18, in another embodiment, is located at the center of the bottom of the blood filter. The gas and blood, which is removed from either gas outlet port 18 is routed back to the venous reservoir of the cardiopulmonary bypass system thus minimizing blood loss during the surgical procedure. The bottom-mounted gas outlet port 18 may be able to take advantage of fluid patterns generated within the shell 12 to enhance separation of gas from the blood.

The diameter of the blood inlet port 20 and the blood outlet port 16 is generally 1.2 cm and ranges from 0.2 cm to 3.0 cm. The diameter of the gas outlet port 18 is from 0.1 cm to 2.0 cm. The diameter of the shell 12 is generally from 1 cm to 30 cm, more preferably from 3 cm to 15 cm and most preferably 5 to 10 cm. The length of the shell 12 ranges from 2 cm to 30 cm. Smaller lengths and diameters of the shell 12 are preferable because the priming volume of the disposable blood filter 10 is minimized with minimized dimensions and a small priming volume reduces patient blood lost during a bypass procedure.

The baffle 22 is a cylindrical structure located inside the conical top of the disposable filter 10 under the gas outlet port 18. The series of vent holes 28 perforate the circumferential periphery of the baffle 22. The diameter of the baffle 22 is optimized to shunt the blood with gas bubbles away from the blood outlet port 16. The length of the baffle 22 is generally such that the lowermost portion of the baffle 22 is at or below the height of the blood outlet port 16. The maximum radius of the baffle 22 is equal to or less than the distance from the innermost extent of the blood outlet port 16 from the center of the shell 12.

The gas outlet port 18 directs gas out of the disposable blood filter 10 and into the gas trap 57 where the small gas bubbles coalesce into macroscopic amounts of gas that is then bled off through the bleed valve 58. The gas trap 57 is, preferably, transparent so that the clinician may monitor the buildup of macroscopic amounts of gas within the gas trap. The bleed valve 58 is either a manual valve, such as a stopcock, or it is an automatic valve that opens when a pre-determined amount of gas builds up within the gas trap 57. The blood and foam collected in the gas trap 57 are preferably returned to a reservoir for recombination with the rest of the blood in the extracorporeal circulation.

The bearing shaft 24 holds the impeller 14 at the center of the bottom inside surface of the shell 12, which is along the central axis of the disposable filter 10. The impeller 14 rotates freely around the bearing shaft 24. The impeller 14 may be designed as a simple axially elongate stirring bar with its axis perpendicular to the axis of the shell 12, like that used by laboratory stirrers. Preferably, the impeller 14 is an axially elongate structure with its axis parallel to that of the shell 12 and a plurality of vanes that engage the blood and force the blood to spin. More preferably, the impeller 14 is a smooth axially elongate cylinder, cone, or other axially elongate shape that rotates and causes the blood to rotate by viscous effects. Such a smooth cylinder is known in the art to move the blood gently, through shear effects, causing minimal damage to blood components such as red cells and leucocytes. In this embodiment, the impeller 14 contains the magnetic coupler 30. The magnetic coupler 30 is preferably a permanent magnet with a north and a south pole which are disposed at diametrically opposed positions on the impeller 14 and distributed so that the center of mass and the center of force is aligned with the rotational central axis of the impeller 14. Typical permanent magnet materials include, but are not limited to, samarium cobalt, neodymium iron boron, ceramics, and the like. A coupling magnet on a drive unit will be similarly configured and will attract opposing polarities on the magnetic coupler 30 in the impeller 14. The magnetic coupler 30 is in one embodiment, embedded and enclosed within the impeller 14. Typical methods of embedding the magnetic coupler 30 include injection molding, insert molding, machining the cavity and inserting the magnetic coupler 30 followed by gluing or bonding a cap over the magnetic coupler 30. The impeller 14 with the magnetic coupler 30 is preferably balanced carefully so that the impeller 14 does not vibrate or wobble when it spins.

The lockdown tabs 46 are located around the bottom outside edge of the cylindrical shell 12 of the disposable filter. Correspondingly, the motor drive 26 has lockdown or clamping mechanisms 44 located around the top outside edge of the cylindrical housing 42. The lockdown tabs 46 mate with the lockdown mechanisms 44 and when the lockdown mechanisms 44 are in the locked position, the disposable filter 10 is attached to the motor drive 26. In order to allow for disposability of the blood handling components, the lock-down or clamping mechanisms 44 permit reversible fastening of the blood filter shell 12 to the motor drive 26. This is important since cross-contamination of patients' blood must be prevented in order to control the spread of infectious diseases. The motor drive 26 may be reusable. In this embodiment, the clamping mechanism 44 is a set of latches that grasp protrusions 46 on shell 12 and hold it to the housing 42 of the motor drive 26. In other embodiments, the clamping mechanism 44 may also be a bayonet mount, spring-loaded catch, magnetic latch or other fastening mechanism.

The motor 32 of the motor drive 26 is affixed to the housing 42. The central shaft 38 is affixed to, and protrudes from, the rotating armature of the motor 32. The motor drive 26 most preferably uses an electric motor 32 powered by a 6 to 24 volt direct current (DC) power supply. Such DC power supplies comprise batteries or electronics to convert alternating current electricity to direct current. The motor 32 could also be designed to use standard 110 VAC to 220 VAC. A direct current power source is preferable to an alternating current power source because patient and hospital staff protection is maximized with the DC system. The motor 32 is powered through the power cable 34. The power switch 36 and the power on light 48 are physically affixed to the housing 42 and electrically connected to the power line 34. The power on light 48 turns on only when the motor 32 is electrically energized by activating the power switch 36. The electric motor 32 spins at a pre-determined constant speed. The central shaft 38 rotates from 100 to 10,000 RPM and most preferably from 500 to 5,000 RPM. Alternative embodiments of the motor 32 include, but are not limited to, compressed air or hydraulically driven motors.

In this embodiment, the magnetic driver 40 is affixed to the shaft 38 and rotates with the shaft 38. The magnetic driver 40 is located near the perimeter of the housing 42 so that when the disposable blood filter 10 is positioned against the motor drive 26, the magnetic driver 40 is magnetically engaged to the magnetic coupler 30 that is affixed to the impeller 14 of the disposable blood filter 10. The motor 32 spins the shaft 38 and the magnetic driver 40. The magnetic driver 40 has a magnetic field that acts through the housing 42 of the motor drive 26 and through the shell 12 of the disposable blood filter 10. The magnetic field interacts with the magnetic coupler 30 in the impeller 14 and causes the impeller 14 to rotate at the same rate as that of the motor 32. The magnetic driver 40 is preferably a bar magnet that spins about its central region with north and south poles diametrically opposed and equidistant from the center of rotation.

The magnetic driver 40 and magnetic coupler 30 may both be permanent magnets. Alternatively, at least one of either the magnetic driver 40 or the magnetic coupler 30 may be permanent magnets with the other being a material that is magnetically attracted to a magnet. In another embodiment, the magnetic coupler 30 or the magnetic driver 40 may be electromagnets energized by batteries or by another type of electrical power supply. Typical permanent magnets are fabricated from materials such as, but not limited to, neodymium iron boron, iron, ceramics, samarium cobalt and the like. Materials that are magnetically attracted to a magnet include, but are not limited to, iron or metallic alloys of iron. The magnetic coupler 30 is desirable because it allows for a sealed disposable blood filter 10 to be attached to the reusable motor drive 26. In an alternate embodiment, a direct coupling between the central shaft 38 and the impeller 14 may be made using interlocking fingers on the impeller 14 that mate with the shaft 38 through a rotary seal.

Attachment of the blood filter assembly 8 to a cardiopulmonary bypass system is accomplished using the optional pole clamp 50. The pole clamp 50 is connected to the housing 42 of the motor drive 26 by the arm 54 and is secured to a pole by the setscrew 52. By attaching the reusable motor drive 26 of the blood filter assembly 8 to a pole or other part of a pump console in the cardiopulmonary bypass system, interchange of the disposable blood filter 10 is more easily accomplished.

Typical materials from which the disposable blood filter shell 12 and baffle 22 are fabricated include polycarbonate, polypropylene, polyethylene, polystyrene, polyvinyl chloride, fluorinated ethylene polymer (FEP), poly tetrafluoroethylene (PTFE), polysulfone, and the like. These same materials are used to fabricate the housing 42 of the motor drive 26, although metals such as aluminum, stainless steel and the like would also work. Optionally, the interior of the shell 12 of the disposable blood filter 10 may be treated with an antithrombogenic material such as heparin and a bonding agent. The impeller 14 is made from materials that include polycarbonate, polypropylene, polyethylene, polystyrene, polyvinyl chloride, fluorinated ethylene polymer (FEP), polysulfone, poly tetrafluoroethylene (PTFE), and the like.

Figure 2A:
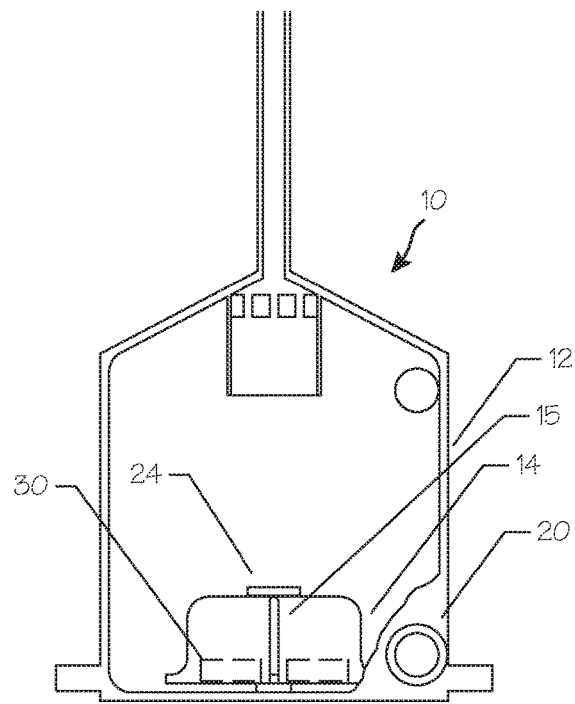
FIG. 2A illustrates a breakaway view of the disposable blood filter of the current invention. An impeller that utilizes vanes is shown in cross-section.

FIG. 2A shows a breakaway view of the shell 12 of the disposable blood filter 10, which comprises the blood inlet port 20 and the impeller 14. The impeller 14 further comprises the bearing shaft 24, the magnetic coupler 30 and a plurality of vanes 15.

Referring to FIG. 2A, the vanes 15 are affixed to, or are integral to, the impeller 14 and appear as fins, rotors or propeller blades. The magnetic coupler 30 is embedded within or affixed to the impeller 14.

The vanes 15 are rotated by the impeller 14, which in turn, is rotated by the magnetic coupler 30 around the bearing shaft 24. The blood enters the shell 12 through the blood inlet port 20 and is rotated by the vanes 15 on the impeller 14.

Figure 2B:
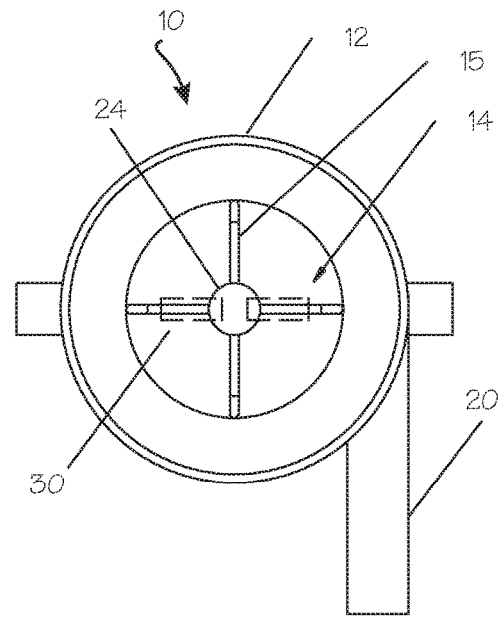
FIG. 2B illustrates a top view of the vane-type impeller through a cross-sectional view of the disposable blood filter of the present invention.

FIG. 2B shows a top cross-sectional view of the shell 12 of the disposable blood filter 10. In this embodiment, the impeller 14 has four vanes 15. Any number of vanes 15 from one to 50 may be employed in the impeller 14. The length and diameter of the vanes 15 are roughly equal to the overall length and diameter of the impeller 14.

FIG. 3A shows an exterior view of the blood filter assembly 8, comprising the disposable blood filter 10 and the motor drive 26, viewing along the axis of the blood inlet port 20 and blood outlet port 16. Also shown in FIG. 3A are the gas outlet port 18, the gas trap 57, the bleed valve 58, the lock-down mechanisms 44, and the lock-down tabs 46 on the shell 12. FIG. 3B shows an exterior view of the blood filter assembly 8, comprising the disposable blood filter 10 and the motor drive 26, viewing perpendicular to the axis of the blood inlet port 20 and the blood outlet port 16. Also shown in FIG. 3B are the gas outlet port 18, the gas trap 57, the bleed valve 58, the lock-down mechanisms 44, and the lock-down tabs 46 on the shell 12. FIGS. 3A and 3B clearly show the tangential disposition of the blood inlet port 20 and the optional tangential disposition of the blood outlet port 16. The blood inlet port 20 is disposed so that blood enters the disposable filter 10 in a direction tangential to the shell 12 to assist with generation of a rotational fluid field within the shell 12.

Figure 4:
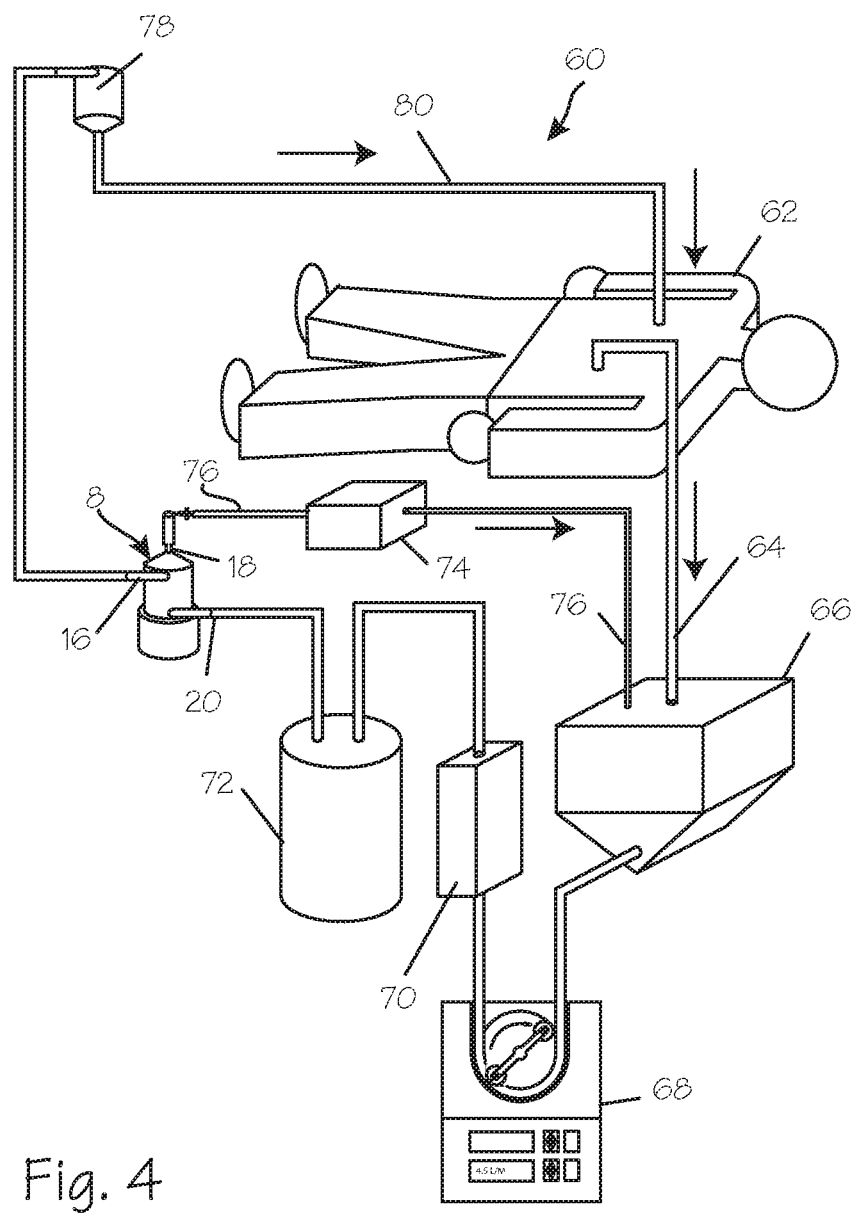
FIG. 4 illustrates a schematic drawing of the cardiopulmonary bypass loop with the blood filter of the current invention in place.

FIG. 4 shows a schematic diagram of a typical cardiopulmonary bypass circuit 60 comprising the blood filter assembly 8 of the present invention. The cardiopulmonary bypass circuit 60 further comprises a patient 62, a venous drainage cannula 64, a venous reservoir 66, a circulatory assist pump 68, a heat exchanger 70, an oxygenator 72, an optional gas pump 74, a gas bleed line 76, a particulate filter 78, and an arterial inlet cannula 80.

The venous circuit of the patient 62 is connected to a blood inlet of the venous reservoir 66 through the venous drainage cannula 64. An outlet of the venous reservoir 66 connects to an inlet of the circulatory assist pump 68 and an outlet of the circulatory assist pump 68 connects to an inlet of the heat exchanger 70. An outlet of the heat exchanger 70 connects to an inlet of the oxygenator 72 and an outlet of the oxygenator 72 connects to the blood inlet port 20 of the blood filter assembly 8. The gas outlet port 18 of the blood filter assembly 8 connects, by way of the gas trap 57 and bleed valve 58, to an inlet of the gas pump 74. An outlet of the gas pump 74 connects to an inlet of the venous reservoir 66 through the gas bleed line 76. The blood outlet port 16 of the blood filter assembly 8 connects to an inlet of the particulate filter 78. An outlet of the particulate filter 78 connects to the patient 62 through the arterial inlet cannula 80.

In yet another embodiment, the disposable blood filter assembly 10 is integrated into the venous reservoir 66 to minimize the need for additional priming volume. Since the venous reservoir 66 holds between 10 cc and 1000 cc of blood, the disposable blood filter 10 may be affixed thereto or integrated therein so that the internal volume of the disposable blood filter 10 does not add significantly to the priming volume of the cardiopulmonary bypass circuitry. In this embodiment, the drive unit or motor drive 26 for the filter 10 attaches to a component of the venous reservoir 66 to rotate the impeller 14 of the blood filter 10. Typically, during cardiopulmonary bypass, venous blood is removed from the patient 62 by the venous drainage cannula 64 and is collected, generally by gravity feed, in venous reservoir 66 where it is de-foamed using standard technology such as de-foaming sponges and bonded surfactants. The venous reservoir 66 generally comprises a blood-air interface and blood entering the reservoir entrains air and other gasses into the blood. In addition, a suction line, used to remove blood from the operative field, returns air and blood to the venous reservoir 66. The de-foaming devices in the venous reservoir 66 are incapable of removing micro-bubbles or small gas bubbles that have become entrained in the blood, thus the need for a blood filter. The blood is pumped from the venous reservoir 66 and through the rest of the cardiopulmonary bypass circuit 60 by the circulatory assist pump 68. The blood passes through the heat exchanger 70 where it is cooled for the majority of the procedure to reduce the metabolic requirements of the patient 62. Typical hypothermia temperatures range from 28 to 35 degrees centigrade. Toward the end of the procedure, the heat exchanger 70 is used to warm the blood to normothermia, approximately 37 degrees centigrade. The blood is next pumped through the oxygenator 72 where it is oxygenated and cleared of carbon dioxide. From the oxygenator 72, the blood is pumped to the blood filter assembly 8.

Referring to FIGS. 1, 3A, 3B, and 4 the blood filter assembly 8 of the present invention is designed to move gas bubbles present in the blood toward the center of the shell 12 so that blood may flow from the outside of the shell 12 through the blood outlet port 16, free of these bubbles. The blood enters the blood filter assembly 8 through the blood inlet port 20. Preferably, the blood inlet port 20 is positioned tangential to the shell 12 of the disposable filter 10. The rotating impeller 14 pushes the blood and causes the blood to rotate. Tangential entry of the blood into the disposable filter 10 imparts a rotational velocity to the blood, thus requiring less shear stress on the blood for the motor 32 to turn the impeller 14 and rotationally accelerate the blood to the required velocity.

The gas bubbles, many as small or smaller than 10 to 25 microns in diameter, need to be moved to the center of the disposable blood filter 10 in the time it takes for the blood to make a single pass through the filter 10. By way of example, a typical blood flow rate through the cardiopulmonary bypass circuit 60 is approximately 5 liters per minute. A typical diameter for the blood filter 10 is 7.5 centimeters. With a 10-centimeter height, the blood filter will have a priming volume of about 440 cubic centimeters. That means blood will dwell within the blood filter 10 for about 5 seconds. The gas bubbles, therefore, have about 5 seconds to move radially inward to within the diameter of the baffle 22 and, thus, be separated from the blood that flows through the blood outlet port 16. Rotational rates specified for this blood filter assembly 8 are sufficient to move bubbles as small as 7 to 10 microns to the center of the blood filter 10 within 5 seconds by means of centrifugal force.

Buoyancy causes the gas bubbles to rise, relative to gravitational attraction, and pass out of the gas outlet port 18 and into the gas trap 57, although the gas removal may be augmented by an optional external pump 74, powered by electricity, for example.

Gas and some blood, removed from the gas outlet port 18 of the disposable blood filter 8 are collected in the gas trap 57 and pumped back into the venous reservoir 66 by optional gas pump 74 through the gas bleed line 76 where the blood component can be reclaimed. The optional gas pump 74 is a continuously operating pump. Optionally, gas pump 74 is a demand pump and pumps only when the volume of gas collects in sufficient quantity to warrant return to the venous reservoir 66. This may be accomplished using a fluid level sensor mounted in the blood filter assembly 8 or gas bleed line 76 that controllably turns power to the gas pump 74 on and off. The bleed valve 58 is optional and not necessary if the gas pump 74 is used.

Referring again to FIG. 4, the blood is pumped from the blood filter assembly 8 through the blood outlet port 16 to the particulate filter 78. The particulate filter 78 may be integral to the blood outlet port 16. The particulate filter 78 filters solid debris and particulates, generally larger than 25 microns, using screens or filter meshes. The oxygenated blood is cleared of most particulates greater than 25 microns and most gas bubbles greater than 7 to 10 microns when it is returned to the patient 62 via the arterial inlet cannula 80.

Figure 5:
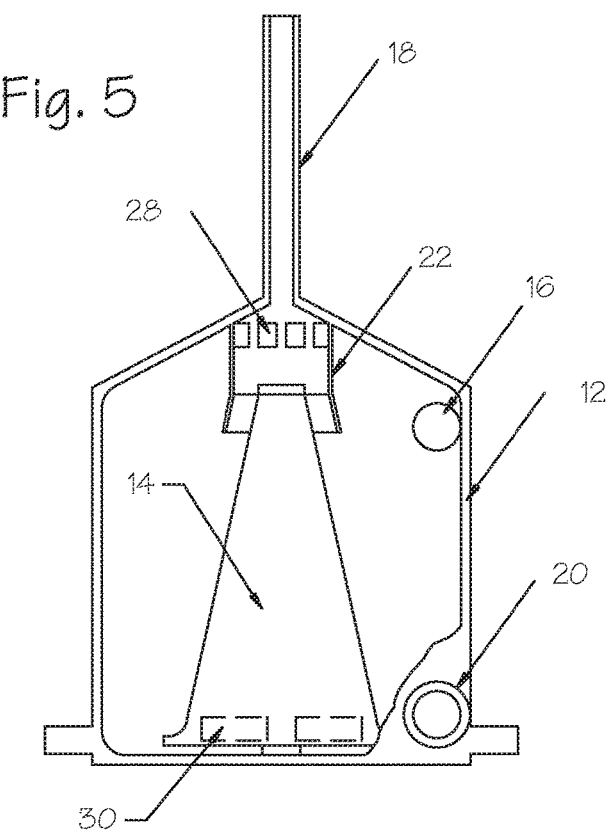
FIG. 5 illustrates a sectional view of another embodiment of the blood filter using a conical impeller with no vanes.

FIG. 5 shows another embodiment of the disposable blood filter 10 wherein the impeller 14 is an axially elongate, smooth shape without any vanes or protrusions. This type of impeller 14 uses viscosity to create shear forces that cause the blood to spin. Referring to FIGS. 1 and 5, the impeller 14 is driven through the magnetic coupler 30 that is adapted to interact with the magnetic driver 40. The preferred shape of the impeller 14 is conical and helps reduce the priming volume of the system. The blood inlet port 20, the blood outlet port 16, and the gas outlet port 18 are disposed in the same configuration as that shown in FIG. 1.

Figure 6:
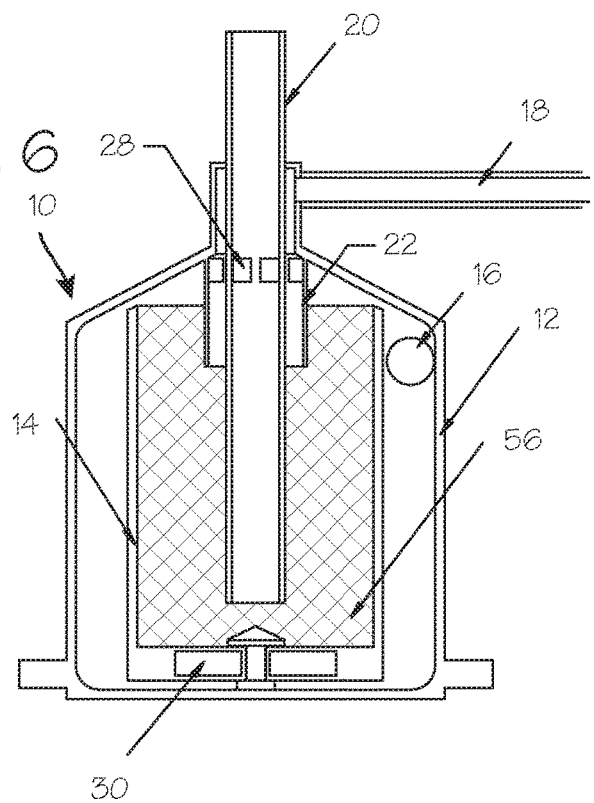
FIG. 6 illustrates a sectional view of another embodiment of the blood filter using an axial inlet port and a screen-type cylindrical impeller.

FIG. 6 shows yet another embodiment of the disposable blood filter 10 wherein the impeller 14 is an axially elongate perforated structure such as a cylinder or cone. The impeller 14, in this embodiment, comprises a filter mesh wall 56. The filter mesh wall 56 is made from a mesh material or screen to provide particulate filtering for the blood that eliminates the need for a secondary particulate filter. The mesh material or screen has a maximum pore size of 25 to 35 microns to limit the size of particulates that can pass through the mesh wall 56.

The blood outlet port 16 is disposed tangential to the shell 12 of the disposable blood filter 10. However, the blood inlet port 20 is disposed along the central axis of the disposable blood filter 10. The blood inlet port 20, optionally, rotates with the impeller 14 to pre-rotate the blood as it enters the filter system and to reduce shear forces acting on the blood at the center of the disposable blood filter 10. The blood enters the filter 10 inside the impeller 14. The gas outlet port 18 is disposed coaxially around the blood inlet port 20 to allow for gas entrapment and removal. The blood outlet port 16 is disposed outside the filter mesh wall 56 of impeller 14 and blood must pass through the filter mesh walls 56 to reach the blood outlet port 16.

In another embodiment, the blood is spun by magnets that directly interact with the ionic potential of the blood. This embodiment requires multiple high output electromagnets that are disposed circumferentially around the perimeter of the disposable blood filter 10. These electromagnets are fired sequentially to form a rotational magnetic field on the blood. A central magnet or a plurality of central magnets is disposed on the core of the disposable blood filter 10 and serves as the alternative pole for the magnets disposed circumferentially around the filter. The blood inlet port 20 and blood outlet port 16 are disposed tangential to the shell 12 of the disposable blood filter 10. The gas outlet port 18 is disposed as close to the axis of the disposable blood filter 10 as possible, given the central magnet structure, at its highest point.

In another embodiment of this device, the blood filter assembly 8 also serves as a primary pump in a cardiopulmonary bypass circuit since centrifugal type pumps are regularly used in a large number of clinical cases. Centrifugal pumps are considered less damaging to the blood than their less-expensive roller-pump alternatives.

In yet another embodiment, the blood filter assembly 8 can be used as a hemoconcentrator. A one-pass hemoconcentrator is useful in separating non-cellular fluids from the cells in the blood at the end of the bypass procedure. The rotational rates of the hemoconcentrator of the current invention will enable such separation of cells. The blood cells are forced to the perimeter of the shell 12 of the disposable blood filter 8 where they are drawn off through the blood outlet port 16. Non-cellular materials, such as plasma, migrate to the center of the filter where the non-cellular materials are drawn out through the central port 18. Rotational spin rates of 1,000 to 20,000 RPM, and more preferably 5,000 to 10,000 RPM, are required to cause adequate centrifugation effects to separate the cellular components from the non-cellular components in a device of 5 to 15 cm diameter.

In a further embodiment, a pressure less than the ambient pressure within the cardiopulmonary bypass circuit 60 is applied to the interior of the disposable blood filter shell 12. The pressure within the cardiopulmonary bypass circuit 60 is, generally, within the range of 0 to 200 mm Hg. By locally reducing the pressure within the blood filter shell 12, the bubble size will be increased and the efficiency of the bubble separation will be likewise increased. The internal pressure within the disposable blood filter 12 is reduced by adding a pump to forcefully remove blood from the interior of the shell 12 through either the blood Outlet port 16 or the gas outlet port 18. Additionally, an optional restriction, or narrowing of the channel, is added to the blood inlet port 20.

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

We claim:

1. A gas removal system for removing gas from a fluid, said system comprising:
 a fluid filter for removing gas bubbles from fluid, said fluid filter comprising:
  a shell defining a chamber characterized by a central axis, a top and bottom;
  an impeller disposed within the chamber;
  a motor operably connected to the impeller,
  a gas vent in fluid communication with the central axis of the chamber and located proximate the top of the chamber,
  a fluid inlet port affixed to the chamber; and
  a fluid outlet port located at the radial periphery of said chamber;
  wherein the impeller is configured to rotate a volume of fluid within the chamber; and
 a pump for forcing fluid through the fluid filter, said pump disposed in fluid communication with the fluid filter.

2. The system of claim 1 wherein:
 the fluid inlet port is located at a radial periphery of the chamber.

3. The system of claim 1 further wherein:
 the fluid inlet port is located at a radial periphery of the chamber at a location lower than the fluid outlet port.

4. The system of claim 1 wherein:
 the fluid inlet port is disposed on the chamber tangentially aligned with the periphery of the chamber, such that fluid enters the chamber in a direction tangential to the shell.

5. The system of claim 1 wherein:
 the fluid outlet port is disposed on the chamber tangentially aligned with the periphery of the chamber, such that fluid exits the chamber in a direction tangential to the shell.

6. The system of claim 1 wherein:
 the impeller is a vaned impeller.

7. The system of claim 1 wherein:
 the impeller is a vaneless impeller.

8. The system of claim 1 wherein:
 the impeller is a cylindrical impeller.

9. The system of claim 1 further comprising:
 a gas pump connected to the gas vent, operable to pump gas from the chamber.

10. A method for removing gas bubbles from a fluid, said method comprising the steps of:
 providing an axially elongate cylindrical shell defining a chamber;
 disposing an impeller within the chamber, wherein the impeller is a smooth-walled cylinder configured to rotate a volume of fluid within the chamber about the central axis of the chamber thus forcing air bubbles within a volume of fluid within the chamber to migrate radially inward in response to centrifugal forces imparted on the volume of fluid by the rotation of said fluid;
 causing fluid to flow into the chamber through a fluid inlet port in the shell, wherein the fluid inlet port is located near the circumferential periphery of the shell;
 rotating the impeller with a motor;
 venting gas from the central axis of the chamber; and
 removing fluid from the chamber through a fluid outlet port in the shell, the fluid outlet port being in fluid communication with the chamber, wherein the fluid outlet port is located near the circumferential periphery of the shell.

11. The method of claim 10 wherein the step of causing fluid to flow into the chamber further comprises the step of:
 operating a pump to force fluid into the chamber.

12. The method of claim 10 further comprising the step of introducing an axially elongate baffle within the chamber to isolate the gas bubbles collected near the centerline of the chamber from gas bubble-free fluid located near the perimeter of the chamber.

13. The method of claim 10 wherein the step of rotating the impeller is performed at a rotational rate of between approximately 100 and 10,000 RPM.

14. The method of claim 10 further comprising the step of operably connecting said gas vent to a gas pump to remove gas from the chamber.

15. The method of claim 10 further comprising the step of magnetically coupling the impeller to the motor, wherein the motor is located externally to the chamber, wherein rotational motion of the motor is imparted to the impeller.

16. The method of claim 10 wherein said fluid inlet port comprises a central axis, which is positioned tangentially to the shell.

17. The method of claim 10 further comprising the step of locating the fluid inlet port higher than said fluid outlet port.

18. The method of claim 10 wherein the fluid outlet port comprises a centerline that is oriented substantially tangential to the shell.

19. The method of claim 10 wherein the chamber is substantially cylindrical between the fluid inlet port, the fluid outlet port, and the impeller.

* * * * *